US 6,584,614 B2

(12) United States Patent
Hogg

(10) Patent No.: US 6,584,614 B2
(45) Date of Patent: Jul. 1, 2003

(54) FACE PROTECTOR

(75) Inventor: John Joseph Hogg, Larkspur, CA (US)

(73) Assignee: John J. Hogg, Larkspur, CA (US)

( * ) Notice: Subject to any disclaimer, the term of this patent is extended or adjusted under 35 U.S.C. 154(b) by 22 days.

(21) Appl. No.: 09/981,066

(22) Filed: Oct. 18, 2001

(65) Prior Publication Data

US 2003/0074708 A1 Apr. 24, 2003

(51) Int. Cl.⁷ .................................................. A61F 9/00
(52) U.S. Cl. .......................................... 2/10; 2/9; 2/432
(58) Field of Search .......................... 2/424, 12, 9, 10, 2/427, 432, 209.13; 351/155

(56) References Cited

U.S. PATENT DOCUMENTS

| 825,288 | A | * | 7/1906 | Ash | 2/10 |
| 1,202,513 | A | * | 10/1916 | Gudger | 2/10 |
| 1,296,366 | A | * | 3/1919 | Clark | 2/10 |
| 1,660,896 | A | * | 2/1928 | Tallman et al. | 2/10 |
| 1,857,284 | A | * | 5/1932 | Nelson | 2/10 |
| 3,035,270 | A | * | 5/1962 | Boerner | 2/10 |
| 3,678,929 | A | * | 7/1972 | Buscher | 2/427 |
| 3,886,596 | A | * | 6/1975 | Franklin et al. | 2/9 |
| 4,063,740 | A | * | 12/1977 | Mader | 2/209.13 |
| 4,975,981 | A | * | 12/1990 | Ray | 2/10 |
| 5,544,361 | A | * | 8/1996 | Fine et al. | 2/10 |
| 5,907,868 | A | * | 6/1999 | Schleger et al. | 2/10 |
| 6,374,424 | B1 | * | 4/2002 | Tredup | 2/427 |

* cited by examiner

Primary Examiner—Rodney M. Lindsey

(57) ABSTRACT

Face Protector with a one piece molded plastic assembly, the assembly comprised of a single plane vertically disposed and radially curved member, the radially curved member shaped to fit around a person's face, the radially curved member terminating in a reinforcing rib about its bottom and side perimeter, the radially curved member terminating at its top edge in an integral, horizontally disposed pocket shaped to fit onto the front portion of a standard baseball cap, said one piece molded assembly molded from a clear, impact resistant material such as polycarbonate, and said molded clear material being treated with an ultraviolet resisting chemical. A preferred embodiment includes wherein said clear material is tinted to reduce eyestrain.

5 Claims, 6 Drawing Sheets

FACE PROTECTOR

BACKGROUND OF THE INVENTION

This invention relates generally to the field of face shields, and more particularly to a face protector that can be removably attached to a baseball cap.

Face protectors of various types are on the market today. They include face shields that are held onto a persons head by elastic straps or other adjustable straps and are used when a person is doing work that may involve items that may fly into the face area of the user. They also include face protectors that are attached to hard hats or the like. Additionally, sunglasses that protect a person's eyes from harmful ultraviolet rays have existed for many years. Baseball caps have also existed for many years and are used to shade the user's eyes from the sun. Recently, the bill portion of baseball caps has become somewhat standardized so that attaching an item to the bill has become more feasible. Although various face shields and sunglass designs are currently available, there is no face protector available that protects the entire face from ultraviolet rays and that can be easily attached to a conventional baseball cap.

SUMMARY OF THE INVENTION

The primary object of the invention is to provide a face protector that fits onto the bill of most baseball type caps.

Another object of the invention is to provide a face protector that blocks ultraviolet rays from hitting the user's face.

Another object of the invention is to provide a face protector that allows a person to wear eyeglasses while also protecting his or her face from ultraviolet rays.

A further object of the invention is to provide a face protector that is molded into a one piece shape.

Other objects and advantages of the present invention will become apparent from the following descriptions, taken in connection with the accompanying drawings, wherein, by way of illustration and example, an embodiment of the present invention is disclosed.

Face Protector comprising: a one piece molded plastic assembly, said assembly comprised of a single plane vertically disposed and radially curved member, said radially curved member shaped to fit around a person's face, said radially curved member terminating in a reinforcing rib about its bottom and side perimeter, said radially curved member terminating at its top edge in an integral, horizontally disposed pocket shaped to fit onto the front portion of a standard baseball cap, said one piece molded assembly molded from a clear, impact resistant material such as polycarbonate, and said molded clear material being treated with an ultraviolet resisting chemical.

The drawings constitute a part of this specification and include exemplary embodiments to the invention, which may be embodied in various forms. It is to be understood that in some instances various aspects of the invention may be shown exaggerated or enlarged to facilitate an understanding of the invention.

DETAILED DESCRIPTION OF THE PREFERRED EMBODIMENTS

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

Figure 1:
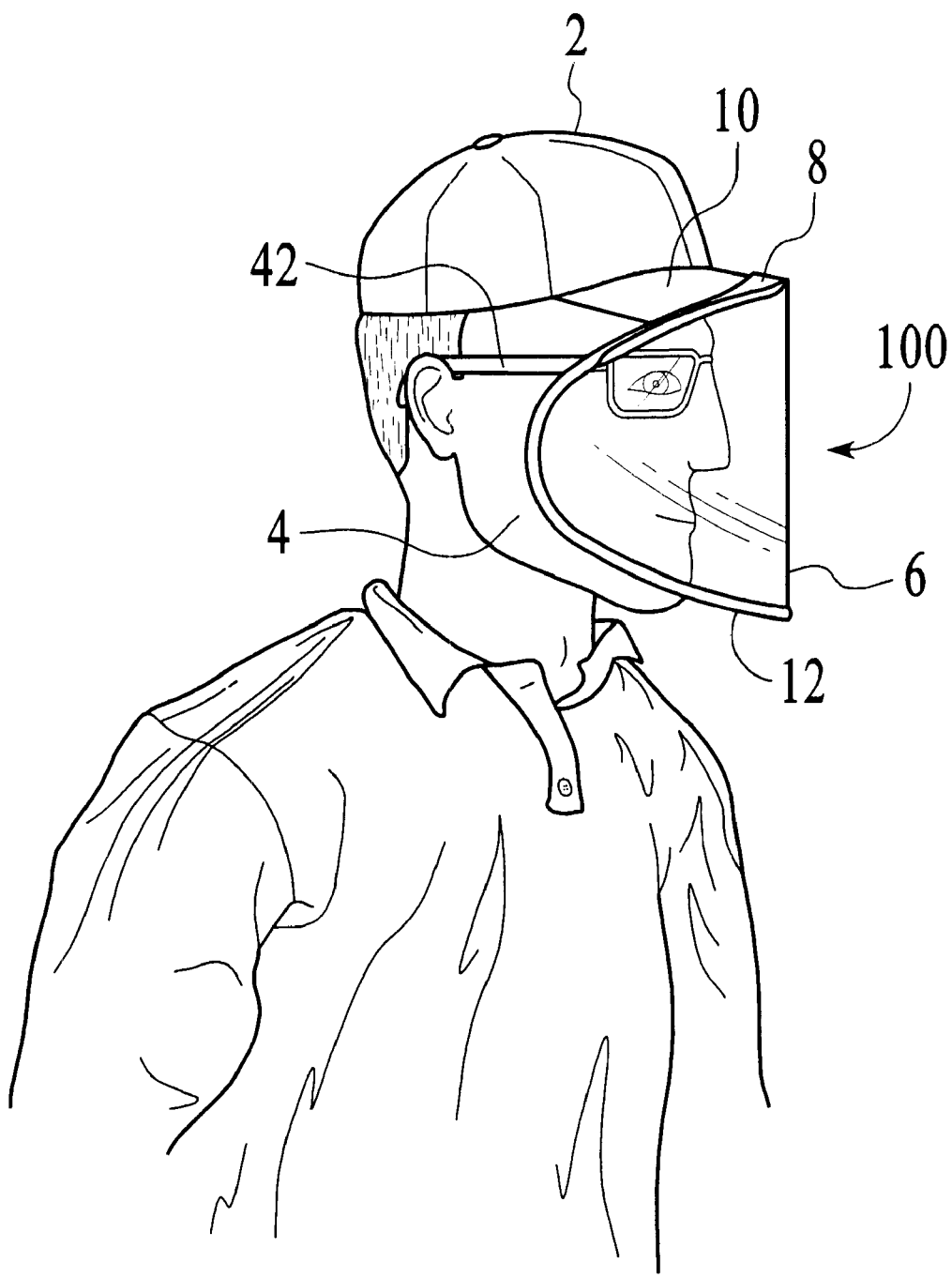
FIG. 1 is a side view of a person wearing the face protector of the present invention.
Figure 2:
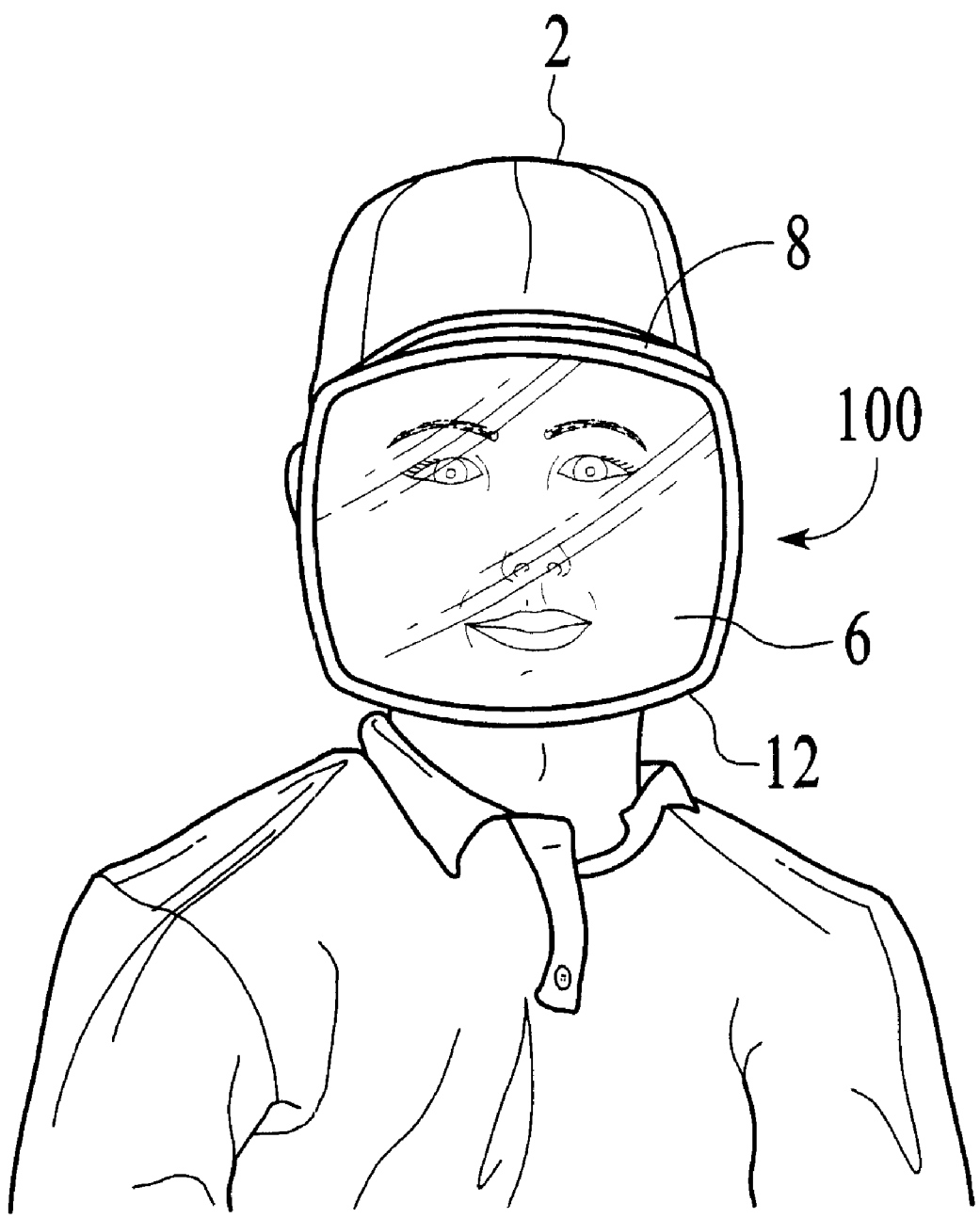
FIG. 2 is a front view of a person wearing the face protector of the present invention.
Figure 3:
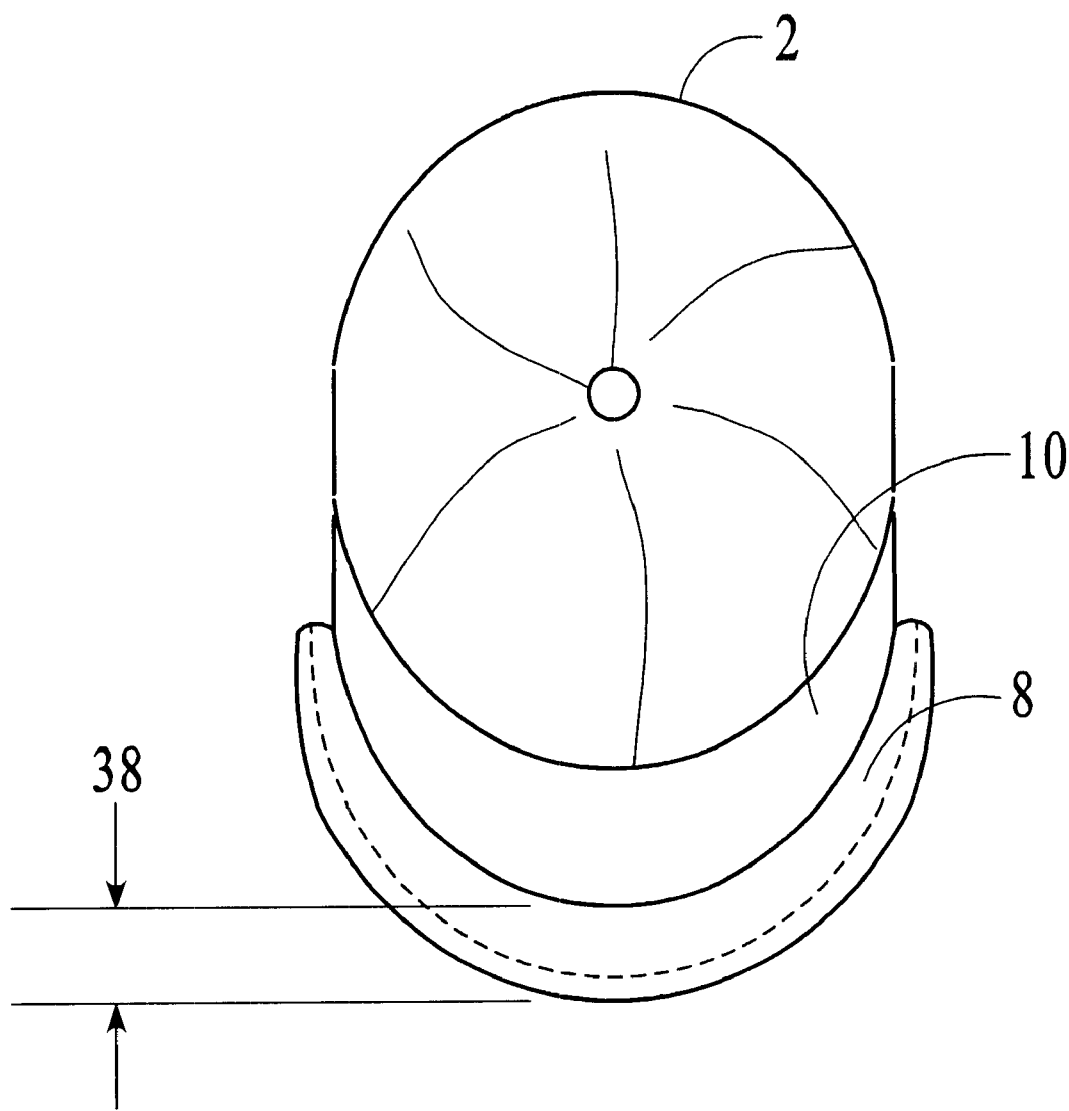
FIG. 3 is a top view the face protector attached to a baseball cap.
Figure 4:
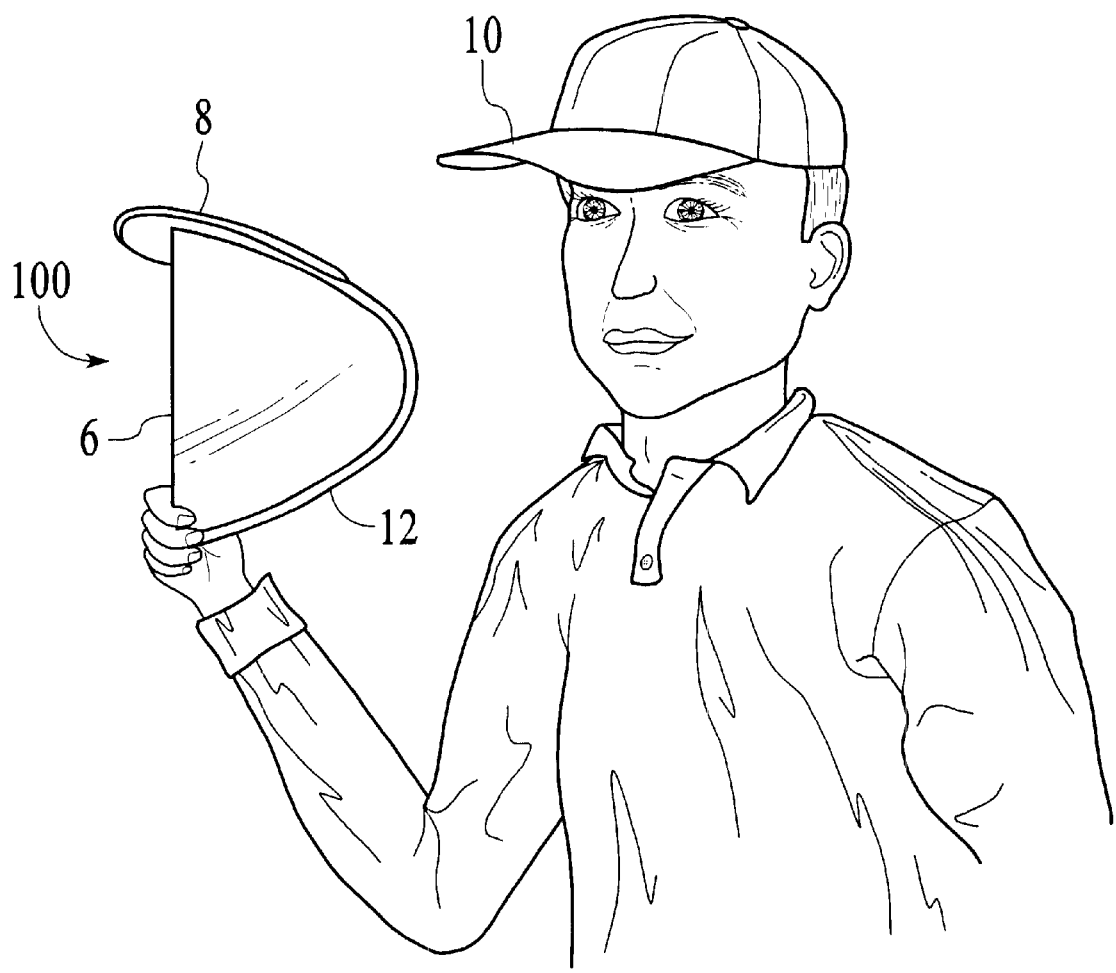
FIG. 4 is a perspective view of a person about to attach the present invention to a baseball cap.
Figure 5:
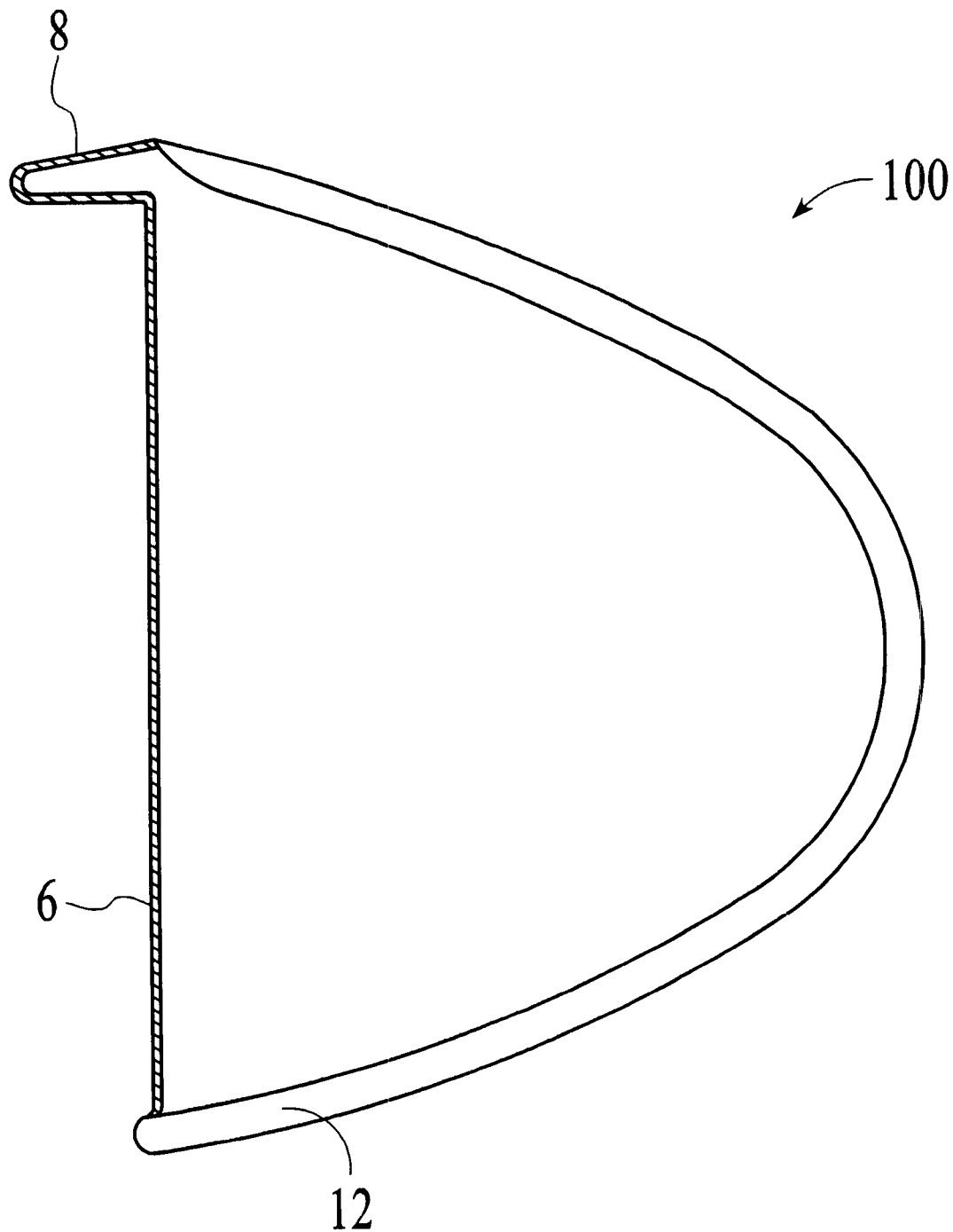
FIG. 5 is a side section view of the present invention
Figure 6:
FIG. 6 is a perspective view of a person wearing the present invention while gardening

Now to FIG. 1 we see a person wearing the face protector 100 of the present invention. The face protector is molded from clear, impact resistant plastic such as polycarbonate and contains within the plastic a chemical that resists ultraviolet rays. The face protector 100 is designed to attach to the bill 10 of a baseball cap 2 by pushing an integral molded pocket 8 onto the bill 10. A radially disposed and vertically oriented sheet of molded plastic forms the main portion the face shield 6. A reinforcing rib 12 surrounds the bottom and side portions of the radial plastic sheet 6. The face protector 100 is far enough away from the users face that a person can wear a pair of conventional eye glasses 42. The radial plastic sheet 6 is large enough to protect the majority of the users face 4 from harmful ultraviolet rays from the sun. The face protector 100 is also far enough away from the users nose, approximately one inch, that the user can breath freely without fogging the radial sheet 6. FIG. 2 shows a front view of the present invention 10. Notice that the face protector 100 covers a majority of the users face. The top pocket 8 that removably attaches to the baseball bill 10 is curved to fit the typical curve of the bill 10. FIG. 3 shows a top view of the invention. Pocket 8 can clearly be seen as it relates to baseball bill 10. My experiments show that pocket 8 needs only be one inch deep 38 for adequate holding, although a deeper pocket may be used. FIG. 4 shows a person about to attach the present invention 100. Because of the one piece construction and the frictional fit of pocket 8 to bill 10, the invention 100 can be quickly added or removed from a standard baseball cap. FIG. 5 shows a side section view of the present invention 100. It can be seen that radial sheet 6 is flat in the vertical plane. Pocket 8 and rib 12 can also be clearly seen. FIG. 6 shows a perspective view of a person gardening and wearing the present invention. It can be clearly seen that the present invention protects the gardener's face from harmful ultraviolet rays while allowing an unobstructed view of the work area. A tinted version of the present invention may also help reduce eyestrain. The tinted version can also be worn by drivers of vehicles. This would allow the driver to have an unobstructed, glare free view of the road even while the driver wears conventional eye glasses.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. Face Protector comprising:

a one piece molded plastic assembly;

said assembly comprised of a single plane vertically disposed and radially curved member;

said radially curved member shaped to fit around a person's face;

said radially curved member terminating in a reinforcing rib about its bottom and side perimeter;

said radially curved member terminating at its top end in an integral, horizontally disposed pocket shaped to fit onto a front most portion of a baseball cap;

said one piece molded assembly molded from a clear, impact resistant material; and said molded clear material being treated with an ultraviolet resisting chemical.

2. Face Protector as claimed in claim 1 wherein said clear material is tinted to reduce eyestrain.

3. Face Protector as claimed in claim 1 wherein said radially curved member is capable of being positioned approximately one inch away from the users nose thereby allowing unobstructed breathing.

4. Face Protector as claimed in claim 1 wherein said radially curved member is employable far enough away from the users face and ears to allow the user to wear conventional eyeglasses while said face protector is being worn.

5. Face protector as claimed in claim 1 wherein said clear material is polycarbonate.

* * * * *